US009924981B2

(12) United States Patent
Harris (10) Patent No.: US 9,924,981 B2
(45) Date of Patent: Mar. 27, 2018

(54) MINIMALLY-INVASIVE SURGERY PEDICLE SCREW AND ROD ASSEMBLY, INSERTER TOOL, AND INSERTION METHOD FOR USE IN SPINAL STABILIZATION PROCEDURES

(71) Applicant: Peter M. Harris, Boca Raton, FL (US)

(72) Inventor: Peter M. Harris, Boca Raton, FL (US)

(73) Assignee: FloSpine LLC, Boca Raton, FL (US)

( * ) Notice: Subject to any disclaimer, the term of this patent is extended or adjusted under 35 U.S.C. 154(b) by 6 days.

(21) Appl. No.: 14/947,040

(22) Filed: Nov. 20, 2015

(65) Prior Publication Data
US 2016/0143674 A1 May 26, 2016

Related U.S. Application Data

(60) Provisional application No. 62/082,175, filed on Nov. 20, 2014.

(51) Int. Cl.
*A61B 17/80* (2006.01)
*A61B 17/70* (2006.01)

(52) U.S. Cl.
CPC ........ *A61B 17/7085* (2013.01); *A61B 17/701* (2013.01); *A61B 17/7011* (2013.01); *A61B 17/7083* (2013.01); *A61B 17/7089* (2013.01)

(58) Field of Classification Search
CPC ............ A61B 17/7032; A61B 17/7037; A61B 17/7035; A61B 17/7002; A61B 17/7053; A61B 2017/564; A61B 17/7083; A61B 17/7041; A61B 17/708; A61B 17/7086; A61B 2017/681; A61B 17/70; A61B 17/7011

See application file for complete search history.

(56) References Cited

U.S. PATENT DOCUMENTS

| 7,497,869 B2* | 3/2009 | Justis | A61B 17/7002 606/279 |
| 2011/0082505 A1* | 4/2011 | Nazeck | A61B 17/7002 606/264 |

* cited by examiner

Primary Examiner — Eduardo C Robert
Assistant Examiner — Tara R Carter
(74) Attorney, Agent, or Firm — Clements Bernard Walker PLLC; Christopher L. Bernard (57) ABSTRACT

The present invention provides a minimally-invasive surgery pedicle screw and rod assembly, inserter tool, and insertion method for use in spinal stabilization procedures and the like. The screw and rod assembly utilizes a screw head body that has a pair of tab extenders that extend longitudinally from the head body to a point well outside of the skin and musculature of the patient. A rod is coupled to and translated along these tab extenders, ultimately into proximity with the head body. The rod is inserted into, aligned with, and translated along the length of the tab extenders, and then selectively pivoted about an enlarged partial spherical bearing into a configuration that is substantially perpendicular to the tab extenders and the head body. The present invention also provides an inserter tool that is used to dispose the rod concentrically within the tab extenders, translate the rod along the length of the tab extenders, and then pivot the rod with respect to the tab extenders and the head body.

10 Claims, 13 Drawing Sheets

MINIMALLY-INVASIVE SURGERY PEDICLE SCREW AND ROD ASSEMBLY, INSERTER TOOL, AND INSERTION METHOD FOR USE IN SPINAL STABILIZATION PROCEDURES

CROSS-REFERENCE TO RELATED APPLICATION

The present patent application/patent claims the benefit of priority of U.S. Provisional Patent Application No. 62/082, 175, filed on Nov. 20, 2014, and entitled "MIS ROD SYSTEM AND METHOD FOR USE IN SPINE STABILIZATION PROCEDURES," the contents of which are incorporated in full by reference herein.

FIELD OF THE INVENTION

The present invention relates generally to the minimally-invasive surgery (MIS) field. More specifically, the present invention relates to a MIS pedicle screw and rod assembly, inserter tool, and insertion method for use in spinal stabilization procedures and the like.

BACKGROUND OF THE INVENTION

A multitude of bone anchor/rod systems exist for affixing adjacent bone segments, such as adjacent levels of the spine in a spinal stabilization procedure, for example. In such procedures, pedicle screws or the like are anchored to the adjacent bone segments. Each pedicle screw has a head body coupled to its head. In a monoaxial configuration, each of these head bodies can rotate with respect to the associated screw head. In a polyaxial configuration, each of the head bodies can rotate and/or pivot with respect to the associated screw head. Once the pedicle screws are anchored to the adjacent bone segments, a rod or the like is disposed in the adjacent head bodies and locked into position using a plurality of set screws or the like, thereby providing rigidity to the overall construct. In either the monoaxial configuration or the polyaxial configuration, these set screws also lock the head bodies to the associated screw heads, thereby preventing further rotation and/or pivoting of the head bodies with respect to the associated screw heads.

This methodology is well known to those of ordinary skill in the art and may be performed via an open procedure or a MIS procedure. In general, an MIS procedure through a portal or the like is preferred, as incision size is minimized, damage to musculature and nerves is minimized, pain is minimized, and recovery time is shortened. Such a MIS procedure, however, presents some significant challenges, as access and visualization is limited. After the pedicle screw or the like are placed, the associated rod must be coupled under the skin and musculature of the patient, and the set screws or the like must be engaged in an accurate and secure manner. It is this rod placement/securement task that is addressed by the assemblies, tools, and methods of the present invention.

BRIEF SUMMARY OF THE INVENTION

In various exemplary embodiments, the present invention provides a MIS pedicle screw and rod assembly, inserter tool, and insertion method for use in spinal stabilization procedures and the like. The screw and rod assembly utilizes a screw head body that has a pair of tab extenders that extend longitudinally from the head body to a point well outside of the skin and musculature of the patient. A rod is coupled to and translated along these tab extenders, ultimately into proximity with the head body. The rod incorporates an enlarged portion that forms a partial spherical bearing that is selectively mated with a partial spherical bearing that runs along the length of the interior of the tab extenders. Thus, the rod can be inserted into, aligned with, and translated along the length of the tab extenders, and then selectively pivoted about the enlarged partial spherical bearing into a configuration that is substantially perpendicular to the tab extenders and the head body. Preferably, this pivoting occurs as the enlarged partial spherical bearing approaches the head body in the tab extenders and is complete when the enlarged partial spherical bearing is disposed entirely within the head body, which also incorporates an interior partial spherical bearing. Finally, an externally-threaded set screw or the like is driven into the head body, which may be internally threaded or the like, thereby driving the enlarged partial spherical bearing of the rod either directly into the screw head or into a locking collar that is then press fit into the head body about the screw head, thereby locking the rod and the head body to the screw head and providing a rigid construct. This screw and rod assembly is described in much greater detail herein below.

In various exemplary embodiments, the present invention also provides an inserter tool that is used to dispose the rod concentrically within the tab extenders, translate the rod along the length of the tab extenders, and then pivot the rod with respect to the tab extenders and the head body. In one exemplary embodiment, the inserter tool includes a squeeze grip and/or trigger that actuates a rod pivoting mechanism at the end of an elongate shaft. The rod pivoting mechanism includes a pair of opposed tines that selectively engage a pair of opposed holes manufactured into one end of the rod adjacent the enlarged partial spherical bearing. The rod pivoting mechanism also includes a pusher rod that selectively engages a channel manufactured into the rod adjacent the pair of opposed holes. The pusher rod is configured to translate longitudinally along the length of the elongate shaft of the inserter tool with respect to the pair of opposed tines when the squeeze grip and/or trigger is actuated, thereby pushing the channel of the rod and rotating the rod about the stationary tines. In another exemplary embodiment, the inserter tool utilizes a button actuation mechanism. In either exemplary embodiment, a splaying mechanism may be used to selectively disengage the pair of opposed tines from the pair of opposed holes of the rod once the proximal end of the rod has been seated in the associated head body and the distal end of the rod has been threaded through an adjacent head body. These inserter tools are described in much greater detail herein below as well.

In one exemplary embodiment, the present invention provides a bone stabilization assembly, including: a bone anchor including a threaded screw including a head, a head body including a pair of opposed tabs coupled to the head of the screw, and a pair of opposed tab extenders selectively extending longitudinally from the pair of opposed tabs of the head body, wherein the pair of opposed tab extenders and the pair of opposed tabs define an internal longitudinal track and a longitudinal slot; and a rod including an enlarged pivot joint at a proximal end thereof and an elongate portion at a distal end thereof, wherein the enlarged pivot joint of the rod is configured to be selectively disposed within and translated along the internal longitudinal track defined by the pair of opposed tab extenders and the pair of opposed tabs and the elongate portion of the rod is configured to selectively protrude through the longitudinal slot defined by the pair of opposed tab extenders and the pair of opposed tabs; wherein, in a first configuration, the rod is distal from the head body and the elongate portion of the rod is disposed longitudinally within the internal longitudinal track defined by the pair of opposed tab extenders, and, in a second configuration, the rod is proximal to the head body and the elongate portion of the rod protrudes substantially perpendicularly from the longitudinal slot defined by the pair of opposed tabs. The rod is pivoted from the first configuration to the second configuration about the enlarged pivot joint as the enlarged pivot joint is translated along the internal longitudinal track and into the head body. The rod is translated along the internal longitudinal track and pivoted using an inserter tool that is selectively coupled to the proximal end of the rod. The inserter tool includes an elongate shaft, and wherein a pair of opposed tines of the inserter tool selectively engage a pair of opposed holes manufactured into the proximal end of the rod and a pusher bar of the inserter tool selectively engages a pusher channel manufactured into the proximal end of the rod adjacent to the pair of opposed holes. The pusher bar of the inserter tool is configured to be selectively translated longitudinally along the elongate shaft with respect to the pair of opposed tines, thereby selectively translating the pusher channel of the rod along the internal longitudinal track with respect to the pair of opposed holes of the rod, thereby causing rotation of the rod about the enlarged pivot joint. In the second configuration, the enlarged pivot joint includes a cross-sectional shape that substantially matches an internal cross-sectional shape of the head body such that it fits conformally therein. The bone stabilization assembly further includes an externally-threaded set screw that is configured to selectively engage internal threads manufactured into the pair of opposed tabs of the head body, thereby biasing the rod into the head of the screw and securing the rod to the head body. The bone stabilization assembly still further includes a retention collar disposed partially between the rod and the head of the screw. The retention collar is press fit into the head body and about the head of the screw when the rod is biased into the head of the screw. In the second configuration, the elongate portion of the rod engages and is subsequently secured to a head body of an adjacent bone anchor.

In another exemplary embodiment, the present invention provides a bone stabilization method, including: disposing a bone anchor in a bone segment, wherein the bone anchor includes a threaded screw including a head, a head body including a pair of opposed tabs coupled to the head of the screw, and a pair of opposed tab extenders selectively extending longitudinally from the pair of opposed tabs of the head body, wherein the pair of opposed tab extenders and the pair of opposed tabs define an internal longitudinal track and a longitudinal slot; and coupling a rod to the bone anchor, wherein the rod includes an enlarged pivot joint at a proximal end thereof and an elongate portion at a distal end thereof, wherein the enlarged pivot joint of the rod is configured to be selectively disposed within and translated along the internal longitudinal track defined by the pair of opposed tab extenders and the pair of opposed tabs and the elongate portion of the rod is configured to selectively protrude through the longitudinal slot defined by the pair of opposed tab extenders and the pair of opposed tabs; wherein, in a first configuration, the rod is distal from the head body and the elongate portion of the rod is disposed longitudinally within the internal longitudinal track defined by the pair of opposed tab extenders, and, in a second configuration, the rod is proximal to the head body and the elongate portion of the rod protrudes substantially perpendicularly from the longitudinal slot defined by the pair of opposed tabs. The rod is pivoted from the first configuration to the second configuration about the enlarged pivot joint as the enlarged pivot joint is translated along the internal longitudinal track and into the head body. The rod is translated along the internal longitudinal track and pivoted using an inserter tool that is selectively coupled to the proximal end of the rod. The inserter tool includes an elongate shaft, and wherein a pair of opposed tines of the inserter tool selectively engage a pair of opposed holes manufactured into the proximal end of the rod and a pusher bar of the inserter tool selectively engages a pusher channel manufactured into the proximal end of the rod adjacent to the pair of opposed holes. The pusher bar of the inserter tool is configured to be selectively translated longitudinally along the elongate shaft with respect to the pair of opposed tines, thereby selectively translating the pusher channel of the rod along the internal longitudinal track with respect to the pair of opposed holes of the rod, thereby causing rotation of the rod about the enlarged pivot joint. In the second configuration, the enlarged pivot joint includes a cross-sectional shape that substantially matches an internal cross-sectional shape of the head body such that it fits conformally therein. The method further includes providing an externally-threaded set screw that is configured to selectively engage internal threads manufactured into the pair of opposed tabs of the head body, thereby biasing the rod into the head of the screw and securing the rod to the head body. The method still further includes providing a retention collar disposed partially between the rod and the head of the screw. The retention collar is press fit into the head body and about the head of the screw when the rod is biased into the head of the screw. In the second configuration, the elongate portion of the rod engages and is subsequently secured to a head body of an adjacent bone anchor.

In a further exemplary embodiment, the present invention provides an inserter tool, including: an elongate shaft; an actuation mechanism coupled to a proximal end of the elongate shaft; and a pivoting mechanism coupled to a distal end of the elongate shaft, wherein the pivoting mechanism includes one or more retention structures configured to selectively pivotably engage one or more corresponding retention structures associated with a proximal end of a rod of a bone stabilization assembly and a pushing structure configured to selectively engages a corresponding pushing structure associated with the proximal end of the rod of the bone stabilization assembly adjacent to the one or more corresponding retention structures; wherein the pushing structure of the inserter tool is configured to be selectively translated longitudinally along the elongate shaft with respect to the one or more retention structures, thereby selectively translating the corresponding pushing structure of the rod with respect to the one or more corresponding retention structures of the rod, thereby causing rotation of the rod with respect to the inserter tool. The bone stabilization assembly includes: a bone anchor including a threaded screw including a head, a head body including a pair of opposed tabs coupled to the head of the screw, and a pair of opposed tab extenders selectively extending longitudinally from the pair of opposed tabs of the head body, wherein the pair of opposed tab extenders and the pair of opposed tabs define an internal longitudinal track and a longitudinal slot; and the rod including an enlarged pivot joint at the proximal end thereof and an elongate portion at a distal end thereof, wherein the enlarged pivot joint of the rod is configured to be selectively disposed within and translated along the internal longitudinal track defined by the pair of opposed tab extenders and the pair of opposed tabs and the elongate portion of the rod is configured to selectively protrude through the longitudinal slot defined by the pair of opposed tab extenders and the pair of opposed tabs; wherein, in a first configuration, the rod is distal from the head body and the elongate portion of the rod is disposed longitudinally within the internal longitudinal track defined by the pair of opposed tab extenders, and, in a second configuration, the rod is proximal to the head body and the elongate portion of the rod protrudes substantially perpendicularly from the longitudinal slot defined by the pair of opposed tabs. The rod is pivoted from the first configuration to the second configuration about the enlarged pivot joint as the enlarged pivot joint is translated along the internal longitudinal track and into the head body. In the second configuration, the enlarged pivot joint includes a cross-sectional shape that substantially matches an internal cross-sectional shape of the head body such that it fits conformally therein. The bone stabilization assembly further includes an externally-threaded set screw that is configured to selectively engage internal threads manufactured into the pair of opposed tabs of the head body, thereby biasing the rod into the head of the screw and securing the rod to the head body. The bone stabilization assembly still further includes a retention collar disposed partially between the rod and the head of the screw. The retention collar is press fit into the head body and about the head of the screw when the rod is biased into the head of the screw. In the second configuration, the elongate portion of the rod engages and is subsequently secured to a head body of an adjacent bone anchor.

BRIEF SUMMARY OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Figure 1:
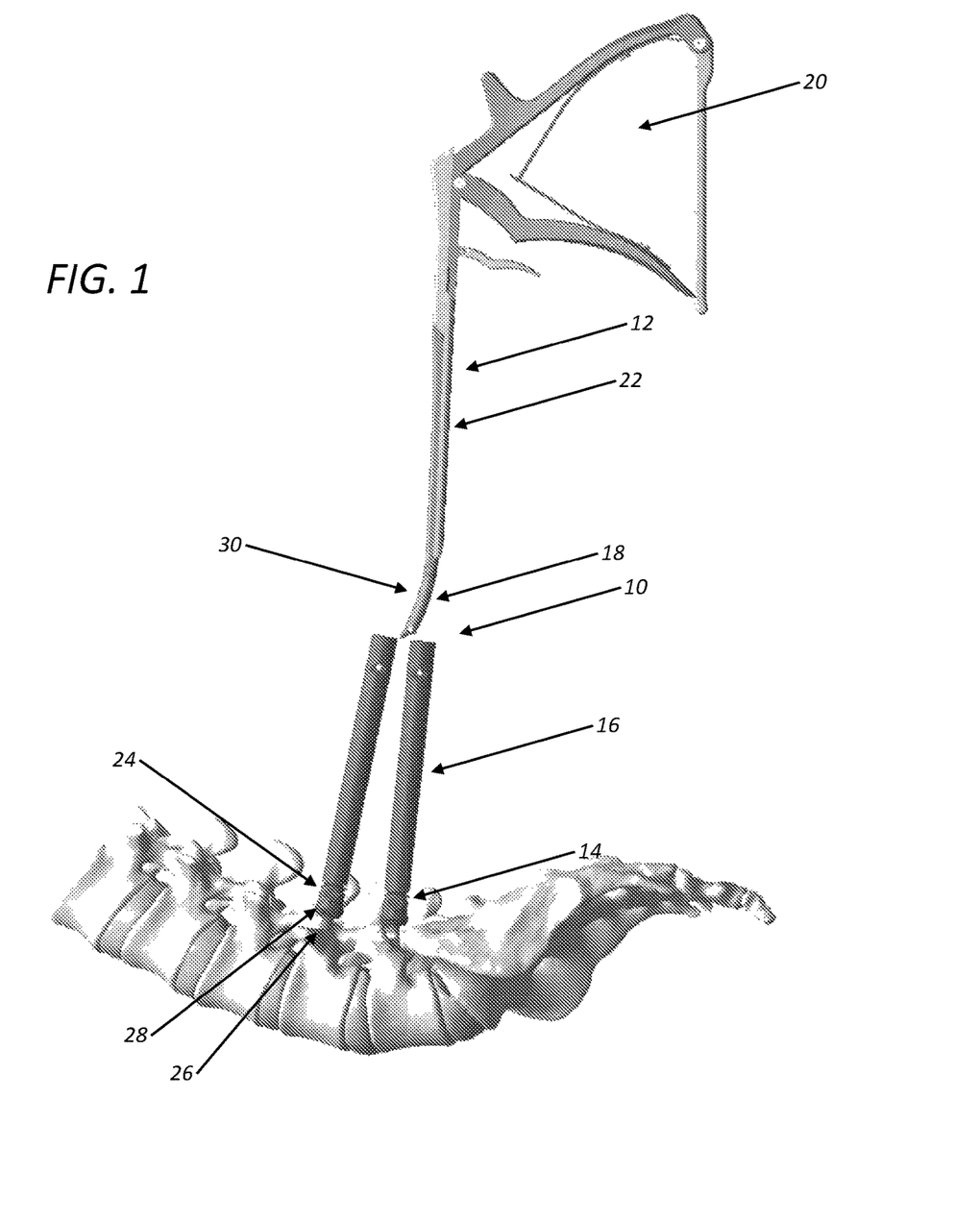
FIG. 1 is a perspective view of one exemplary embodiment of the MIS bone anchor and rod assembly and inserter tool of the present invention, incorporating a plurality of pedicle screws and tab extenders.

Referring now specifically to FIG. 1, in one exemplary embodiment, the present invention provides a MIS pedicle screw and rod assembly 10, inserter tool 12, and insertion method for use in spinal stabilization procedures and the like. The screw and rod assembly 10 utilizes a screw head body 14 that has a pair of tab extenders 16 that extend longitudinally from the head body 14 to a point well outside of the skin and musculature of the patient. A rod 18 is coupled to and translated along these tab extenders, ultimately into proximity with the head body 14. The rod 18 incorporates an enlarged portion that forms a partial spherical bearing that is selectively mated with a partial spherical bearing that runs along the length of the interior of the tab extenders 16. Thus, the rod 18 can be inserted into, aligned with, and translated along the length of the tab extenders 16, and then selectively pivoted about the enlarged partial spherical bearing into a configuration that is substantially perpendicular to the tab extenders 16 and the head body 14. Preferably, this pivoting occurs as the enlarged partial spherical bearing approaches the head body 14 in the tab extenders 16 and is complete when the enlarged partial spherical bearing is disposed entirely within the head body 14, which also incorporates an interior partial spherical bearing. Finally, an externally-threaded set screw or the like is driven into the head body 14, which may be internally threaded or the like, thereby driving the enlarged partial spherical bearing of the rod 18 either directly into the screw head or into a locking collar that is then press fit into the head body 14 about the screw head, thereby locking the rod 18 and the head body 14 to the screw head and providing a rigid construct. This screw and rod assembly 10 is described in much greater detail herein below.

In various exemplary embodiments, the present invention also provides an inserter tool 12 that is used to dispose the rod 18 concentrically within the tab extenders 16, translate the rod 18 along the length of the tab extenders 16, and then pivot the rod 18 with respect to the tab extenders 16 and the head body 14. In one exemplary embodiment, the inserter tool includes a squeeze grip and/or trigger 20 that actuates a rod pivoting mechanism at the end of an elongate shaft 22. The rod pivoting mechanism includes a pair of opposed tines that selectively engage a pair of opposed holes manufactured into one end of the rod 18 adjacent the enlarged partial spherical bearing. The rod pivoting mechanism also includes a pusher rod that selectively engages a channel manufactured into the rod 18 adjacent the pair of opposed holes. The pusher rod is configured to translate longitudinally along the length of the elongate shaft 22 of the inserter tool 12 with respect to the pair of opposed tines when the squeeze grip and/or trigger 20 is actuated, thereby pushing the channel of the rod 18 and rotating the rod 18 about the stationary tines. In another exemplary embodiment, the inserter tool 12 utilizes a button actuation mechanism. In either exemplary embodiment, a splaying mechanism may be used to selectively disengage the pair of opposed tines from the pair of opposed holes of the rod 18 once the proximal end of the rod 18 has been seated in the associated head body 14 and the distal end of the rod 18 has been threaded through an adjacent head body 14. These inserter tools 12 are described in much greater detail herein below as well.

In one exemplary embodiment, the bone anchor and rod assembly 10 includes a bone anchor 24 consisting of a bone screw 26 (such as a pedicle screw or the like) having a head 28 and a head body 14 coupled to the head 28 of the bone screw 26. In general, this bone anchor 24 resembles a multitude of other conventional bone anchors, in that it is driven into a bone segment and the head body 14 may be monoxial or polyaxial until it is locked into place, typically by placing a rod 18 and driving a set screw or the like into the recess and/or saddle of the head body 14 and onto the rod 18. Accordingly, the head body 14 may be internally threaded and the set screw may be externally threaded. It will be readily apparent to those of ordinary skill in the art that many different types of bone anchors may be used equally with the other concepts and techniques of the present invention. This exemplary bone anchor 24 is described in much greater detail herein below.

A pair of concentrically-arranged tab extenders 16 extend from the top of each head body 14 to a point well above the skin and musculature of the patient when in use. Preferably, these tab extenders 16 are externally threaded at the bottom and engage corresponding internal threads of the head bodies 14, or are otherwise removably coupled to the head bodies 14, such that they may be removed at the completion of a surgical procedure. Optionally, the tab extenders 16 are internally threaded, at least at the bottom, and this internal threading matches that of the head body 14, such that the set screw may ultimately be driven down through the tab extenders 16 and into the head body 14, where it ultimately compresses the rod 18 and locks the head body into alignment and in place. Each pair of tab extenders 16 collectively define an internal channel that runs longitudinally along the length of the pair of tab extenders 16. This internal channel acts as a partial spherical bearing surface and allows an appropriate object disposed within the internal channel to pivot. This internal channel also acts as a track or rail along which the sliding, pivoting rod 18 is translated, from the top of the tab extenders 16 into the head body 14. This functionality is described in much greater detail herein below. Each pair of tab extenders 16 also collectively define at least one slot that runs longitudinally along the length of the pair of tab extenders 16, from the top to the head body 14. This slot acts as a through which the elongate portion 30 of the sliding, pivoting rod 18 ultimately protrudes. This functionality is also described in much greater detail herein below. Accordingly, the rod 18 is disposed longitudinally within the internal channel of the tab extenders 16 and translated along the tab extenders 16 towards the head body 14. Near the head body 14, the elongate portion 30 of the rod 18 is pivoted out of the tab extenders 16, through the slot, as the rod 18 engages the head body 14 in a substantially perpendicular alignment thereto. The elongate portion 30 of the rod 18 simultaneously engages the head body 14 of an adjacent bone anchor 24 that has been secured to an adjacent bone segment. The rod 18 is then secured to both head bodies 14 in a conventional manner. Again, this functionality is described in much greater detail herein below.

Figure 2:
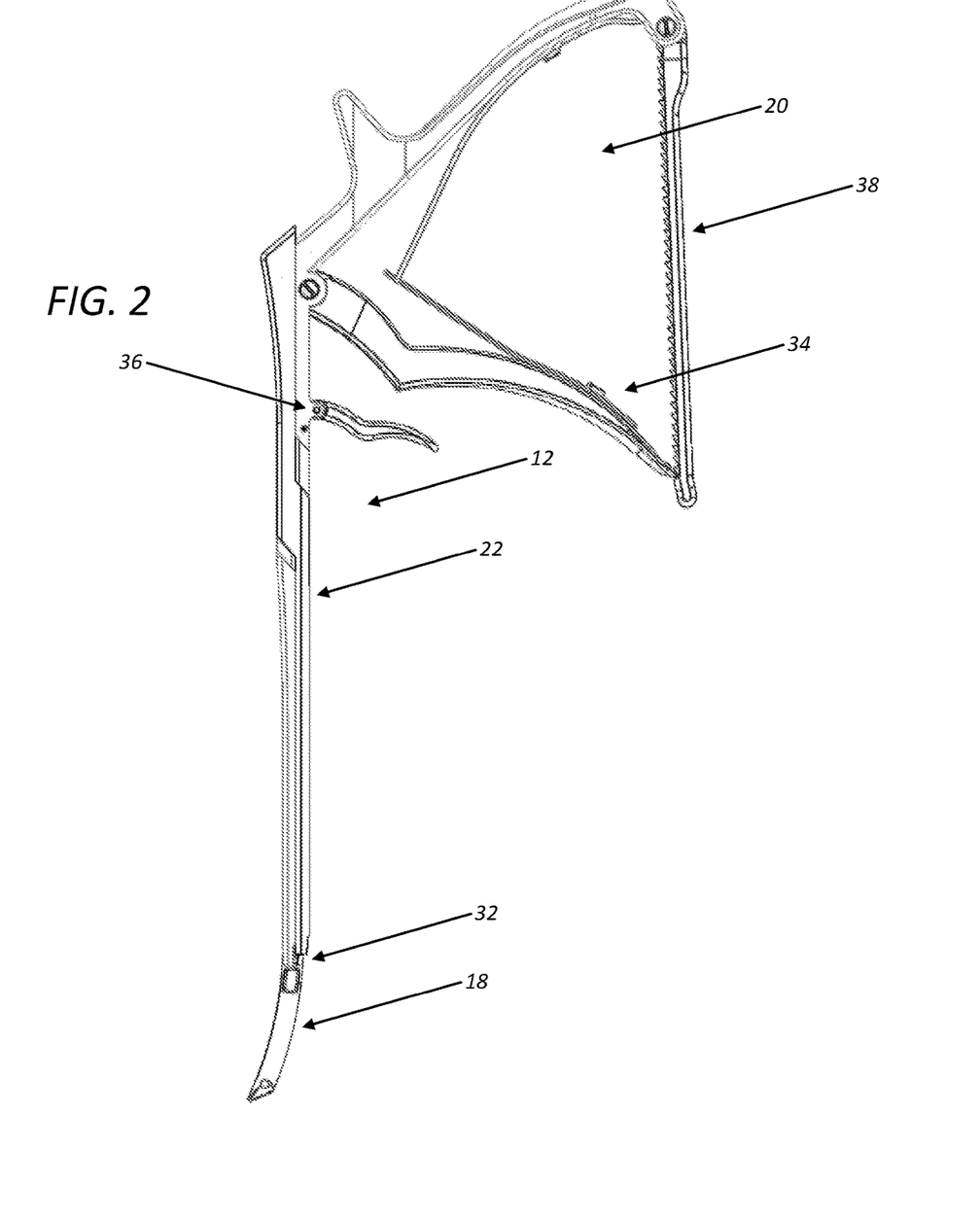
FIG. 2 is a planar view of one exemplary embodiment of the inserter tool of the present invention, coupled to a rod of the present invention.

Referring now specifically to FIG. 2, in one exemplary embodiment, the inserter tool 12 includes an elongate shaft 22 with an actuation mechanism 20 coupled to a proximal end thereof and a pivoting mechanism 32 coupled to a distal end thereof. The pivoting mechanism 32 is selectively coupled to a proximal end of a rod 18 and selectively pivots the rod 18 about its proximal end when the actuation mechanism 20 is actuated and/or releases the proximal end of the rod 18 when the actuation mechanism 20 is actuated, as is described in much greater detail herein below. In this exemplary embodiment, the actuation mechanism 20 includes a spring-loaded ratcheting mechanism 34 that pivots the rod 18 when squeezed and a trigger mechanism 36 that releases the rod 18 when pulled. The spring-loaded ratcheting mechanism 34 can include a locking mechanism 38 or the like, as desired.

Figure 3:
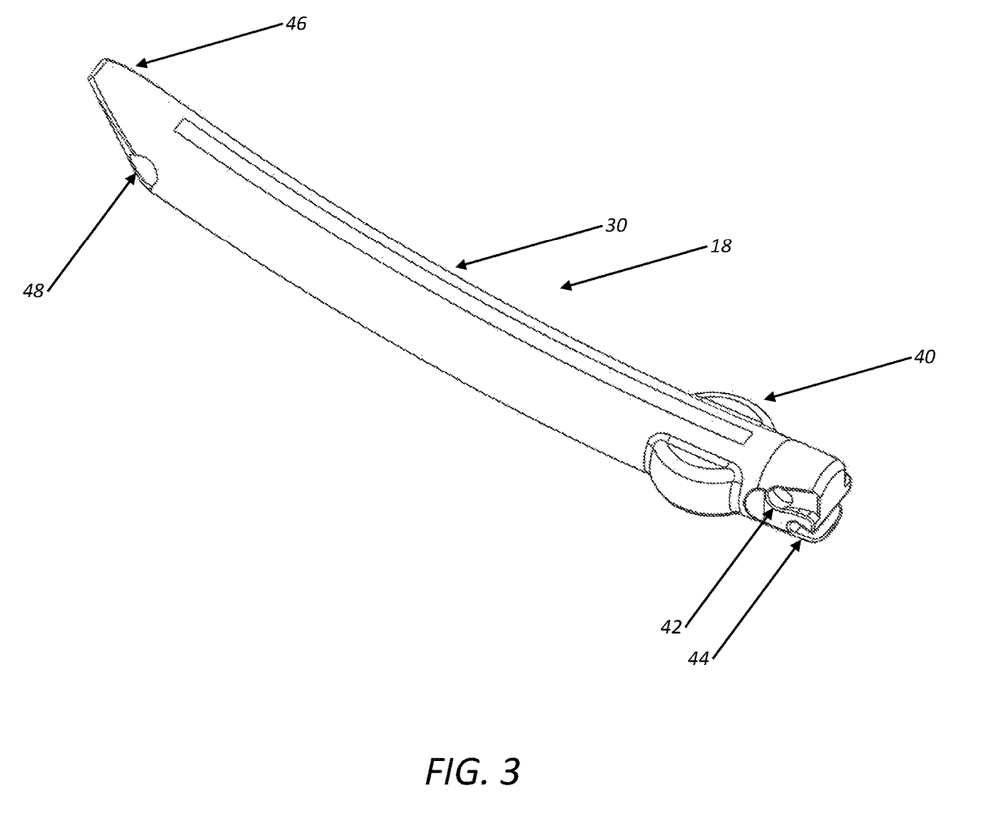
FIG. 3 is a perspective view of one exemplary embodiment of the rod of the present invention, highlighting the enlarged partial spherical bearing portion.
Figure 4:
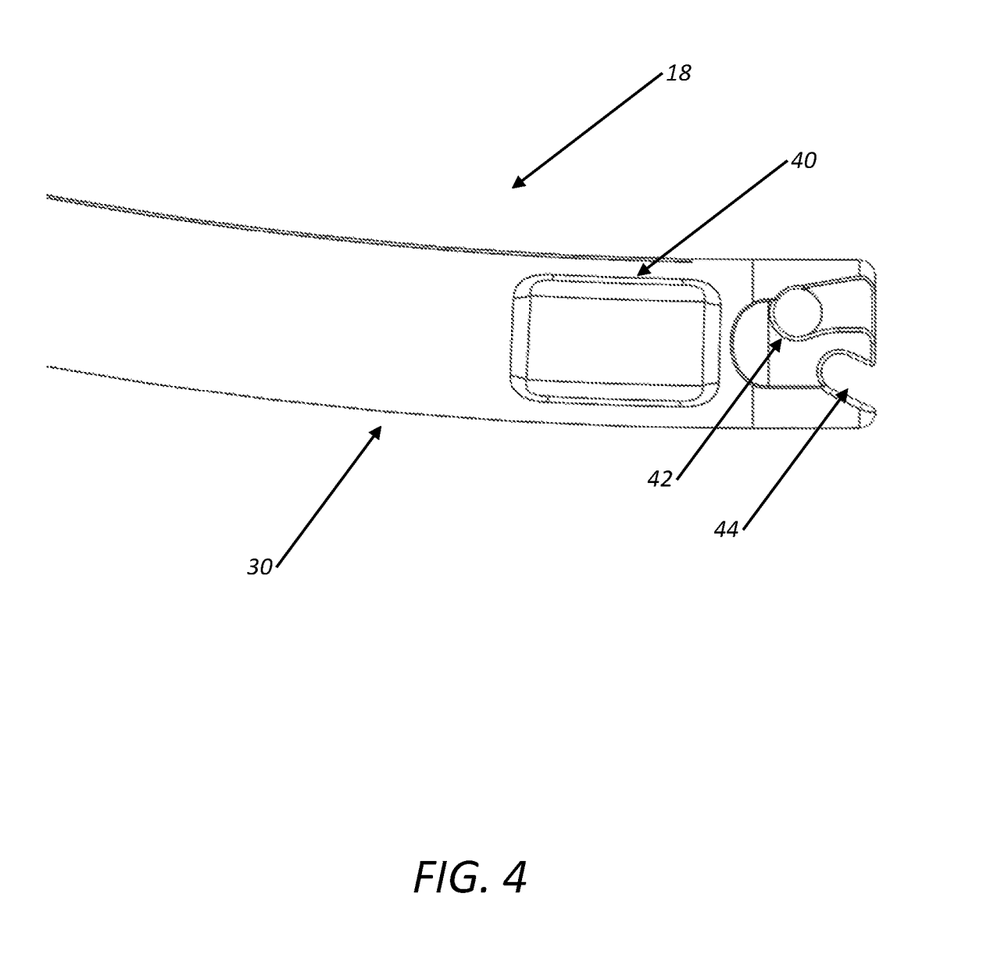
FIG. 4 is a partial planar view of one exemplary embodiment of the rod of the present invention, highlighting the inserter tool engagement portion.

Referring now specifically to FIGS. 3 and 4, in one exemplary embodiment, the rod 18 includes an elongate portion 30 that makes up the majority thereof. The proximal end of the rod 18 includes a plurality of structures that are designed to receive a plurality of corresponding structures of the retention and pivoting mechanisms 32 of the inserter tool 12 and an enlarged partial spherical bearing 40 by which the rod 18 engages the tab extenders 16 of the bone anchor 24 and pivots. Specifically, the proximal end of the rod 18 includes a pair of opposed holes 42 that are configured to be selectively engaged by a corresponding pair of opposed tines of the inserter tool 12 and about which the rod 18 is selectively pivoted. The proximal end of the rod 18 also includes a pusher channel 44 that is configured to be selectively engaged by a corresponding pusher structure of the inserter tool 12. When this pusher channel 44 is translated longitudinally with respect to the pair of opposed holes 42, the rod 18 pivots about the pair of opposed tines. Conceptually, the partial spherical bearing 40 represents a disc-shaped structure that traverses the body of the rod 18. The partial spherical bearing 40 has rounded edges, such that the partial spherical bearing 40 can be disposed longitudinally within the internal channel defined by the tab extenders 16 and tabs of the head body 14 and the rod 18 can translate longitudinally along the internal channel defined by the tab extenders 16 and tabs of the head body 14. The partial spherical bearing 40 can also be rotated within the internal channel, coincident with the pivoting of the rod 18, all without undesirable binding. Accordingly, the internal surfaces of the tab extenders 16 and tabs of the head body 14 form a corresponding partially cylindrical or spherical bearing in which the partial spherical bearing 40 of the rod 18 can translate and pivot. The tab extenders 16 and tabs of the head body 14 may thus consist of concave structures that collectively define the majority of a hollow tube or the like. Finally, the partial spherical bearing 40 is shaped such that it may ultimately conformally nest within the internal void of the head body 14, adjacent to the head 28 of the screw 26. The distal end of the rod 18 includes a tapered end 46 that aides in the insertion of the elongate portion 30 of the rod 18 into and through the adjacent head body 14 when the rod 18 is pivoted and deployed through the slot formed by the tab extenders 16 and the tabs of the head body 14. The tapered end 46 or any other portion of the rod 18 (and/or any other components of the bone anchor and rod assembly 10) may also include any manner of holes 48 or other markings that may be visualized during a surgical procedure, by eye or under fluoroscopy. For example, the hole 48 at the tapered end 46 of the rod 18 can be visualized to determine whether or not the rod 18 has sufficiently penetrated through the adjacent head body 14 when deployed.

Figure 5:
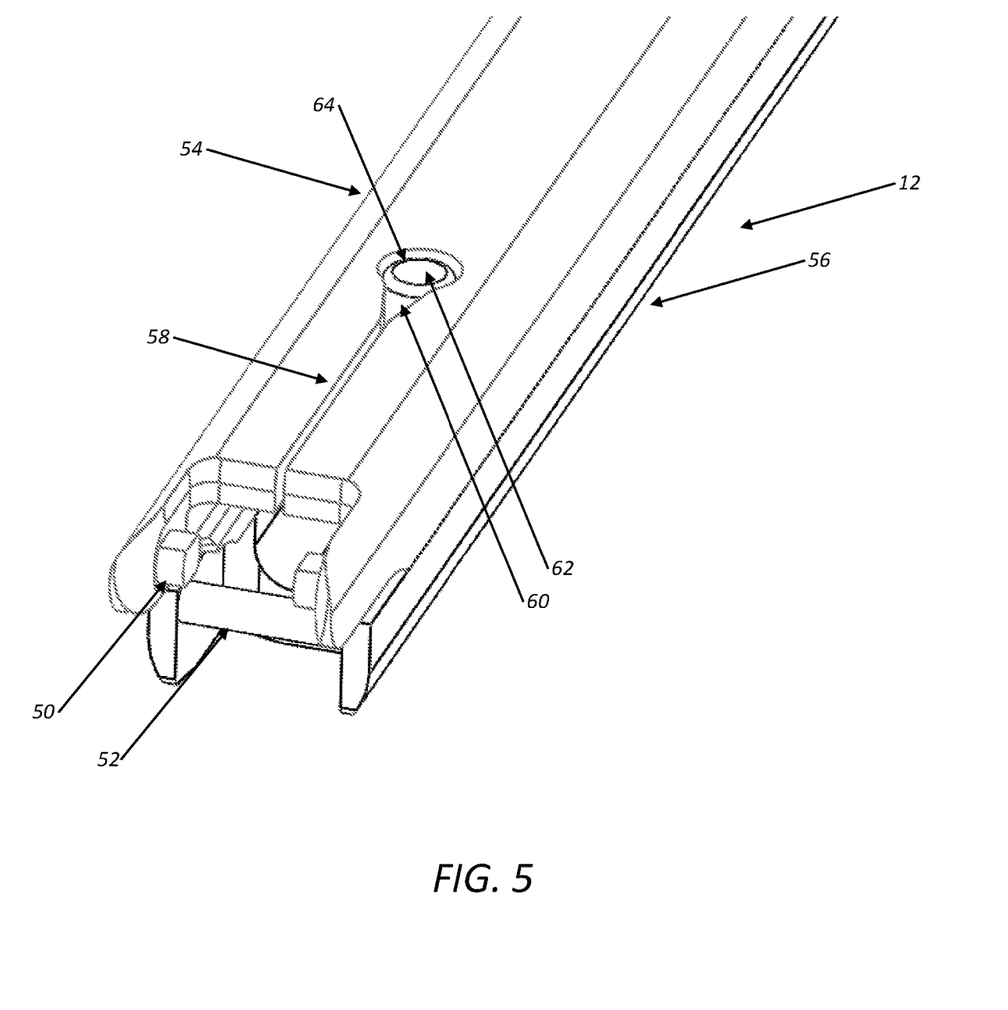
FIG. 5 is a partial perspective view of one exemplary embodiment of the inserter tool of the present invention, highlighting the rod engagement portion and splaying release mechanism.
Figure 6:
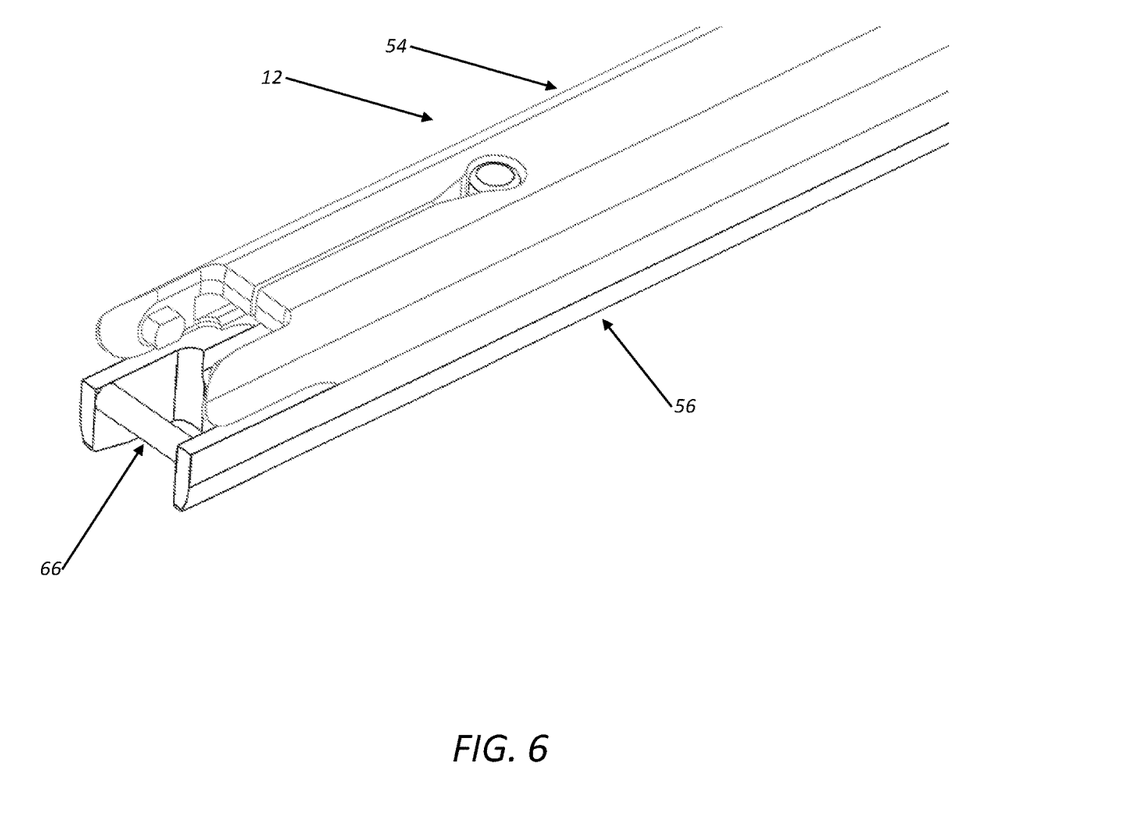
FIG. 6 is a partial perspective view of one exemplary embodiment of the inserter tool of the present invention, highlighting the rod engagement portion in an actuated configuration and splaying release mechanism.

Referring now specifically to FIG. 5, in one exemplary embodiment, the distal end of the inserter tool 12 includes a pair of opposed tines 50 that are configured to selectively engage the pair of opposed holes 42 about which the rod 18 is selectively pivoted. The distal end of the inserter tool 12 also includes a pusher structure 52 that is configured to selectively engage the pusher channel 44 of the rod 18. Preferably, the elongate shaft 22 of the inserter tool 12 consists of a pair of parallel members 54 and 56 that are configured to translate longitudinally with respect to one another via actuation of the actuation mechanism 20. The pair of opposed tines 50 are coupled to one of the parallel members 54 and the pusher structure is coupled to the other of the parallel members 56, such that the pair of opposed tines 50 and the pusher structure 52 are configured to translate longitudinally with respect to one another via actuation of the actuation mechanism 20. When the pusher structure 52 and pusher channel 44 of the rod 18 are translated longitudinally with respect to the pair of opposed tines 50 and the pair of opposed holes 42 of the rod 18, the rod 18 pivots about the pair of opposed tines 50. The parallel member 54 with the pair of opposed tines 50 typically has a spilt 58 at the end thereof, separating the pair of opposed tines 50. This split 58 is integral with a ramped recess 60 and a hole 62 through which a post 64 protrudes. When this post 64 is forced from the hole 62 into the ramped recess 60, the separation of the split 58 is increased, thereby increasing the separation between the pair of opposed tines 50. Conversely, when the post 64 is allowed to return from the ramped recess 60 to the hole 62, the separation of the split 58 is decreased, thereby decreasing the separation between the pair of opposed tines 50. This acts as a catch/release mechanism for the rod 18, via actuation of the trigger mechanism 36, for example. Either the first parallel member 54 is selectively translated with respect to the post 64, or the post 64 is translated with respect to the first parallel member 54. FIG. 6 illustrates this splaying mechanism 66 is a retention configuration, with the second parallel member 56 being translated to pivot the rod 18.

Figure 7:
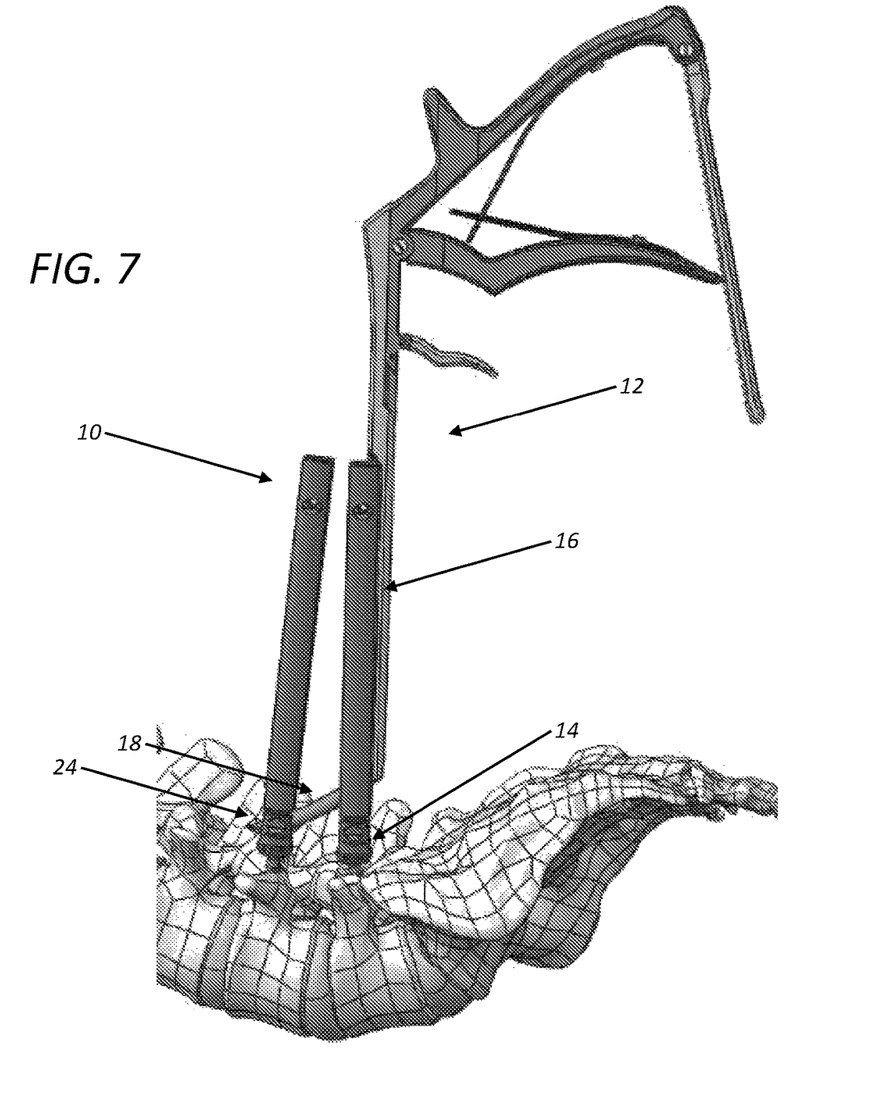
FIG. 7 is a perspective view of one exemplary embodiment of the MIS bone anchor and rod assembly and inserter tool of the present invention, incorporating a plurality of pedicle screws and tab extenders in a partially actuated configuration.

FIG. 7 is a perspective view of one exemplary embodiment of the MIS bone anchor and rod assembly 10 and inserter tool 12 of the present invention, incorporating a plurality of pedicle screws 24 and tab extenders 16 in a partially actuated configuration, with the rod 18 near the bottom of the associated tab extender 16 near the head body 14 and partially pivoted into the adjacent head body 14.

Figure 8:
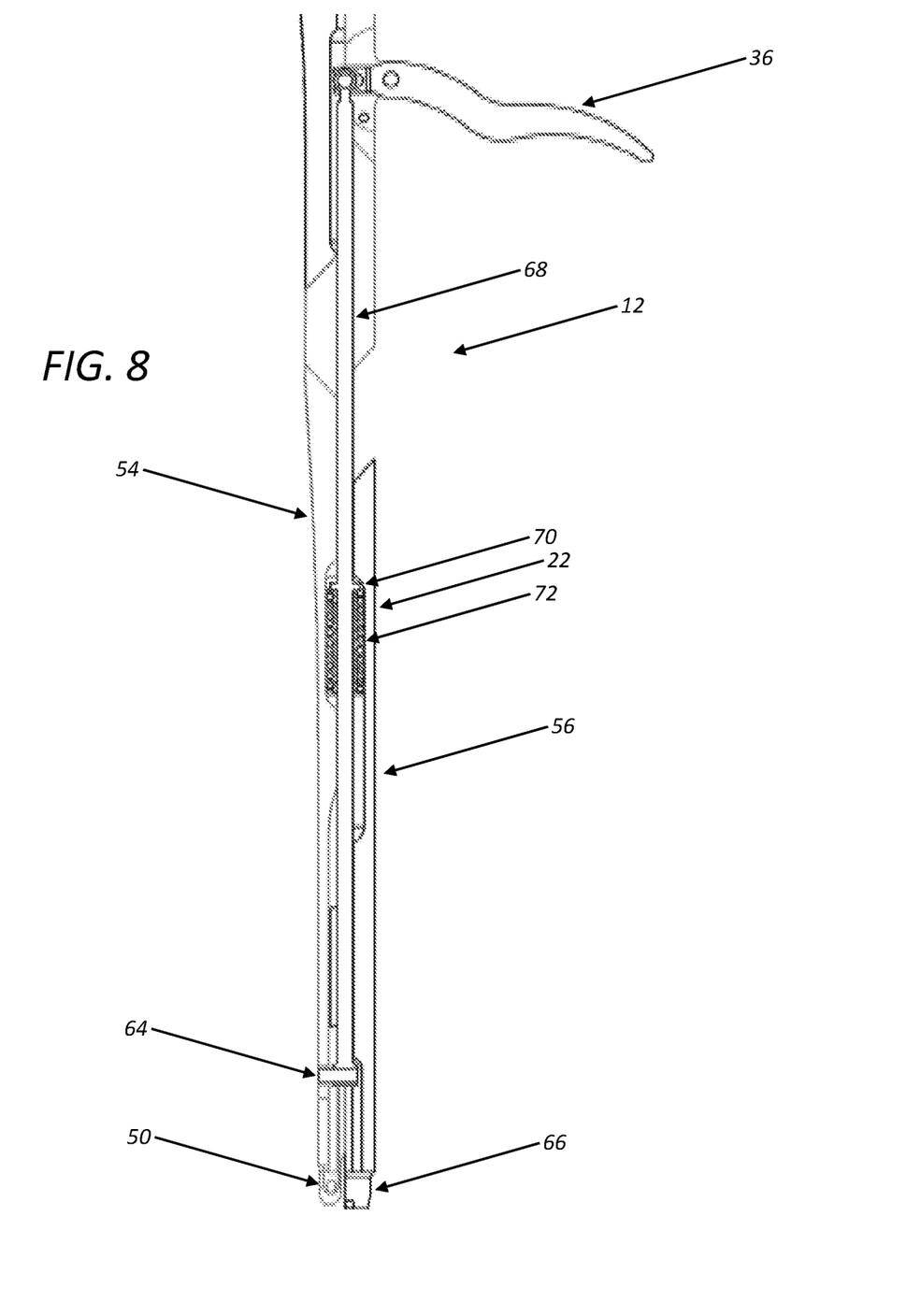
FIG. 8 is a partial cross-sectional view of one exemplary embodiment of the inserter tool of the present invention, highlighting the actuation of the splaying release mechanism.

Referring now specifically to FIG. 8, in one exemplary embodiment, the parallel member 54 with the pair of opposed tines 50 again has a spilt 58 at the end thereof, separating the pair of opposed tines 50. This split 58 is integral with a ramped recess 60 and a hole 62 through which the post 64 protrudes. When the post 64 is forced from the hole 62 into the ramped recess 60, the separation of the split 58 is increased, thereby increasing the separation between the pair of opposed tines 50. Conversely, when the post 64 is allowed to return from the ramped recess 60 to the hole 62, the separation of the split 58 is decreased, thereby decreasing the separation between the pair of opposed tines 50. This acts as a catch/release mechanism for the rod 18, via actuation of the trigger mechanism 36. In this exemplary embodiment, the trigger mechanism 36 is coupled to the post 64 via a strut 68 having an intermediate shoulder 70 that is biased by a spring 72. Thus, the post 64 is selectively pushed into the splay mechanism 66, but is biased to return to its original neutral position.

Figure 9:
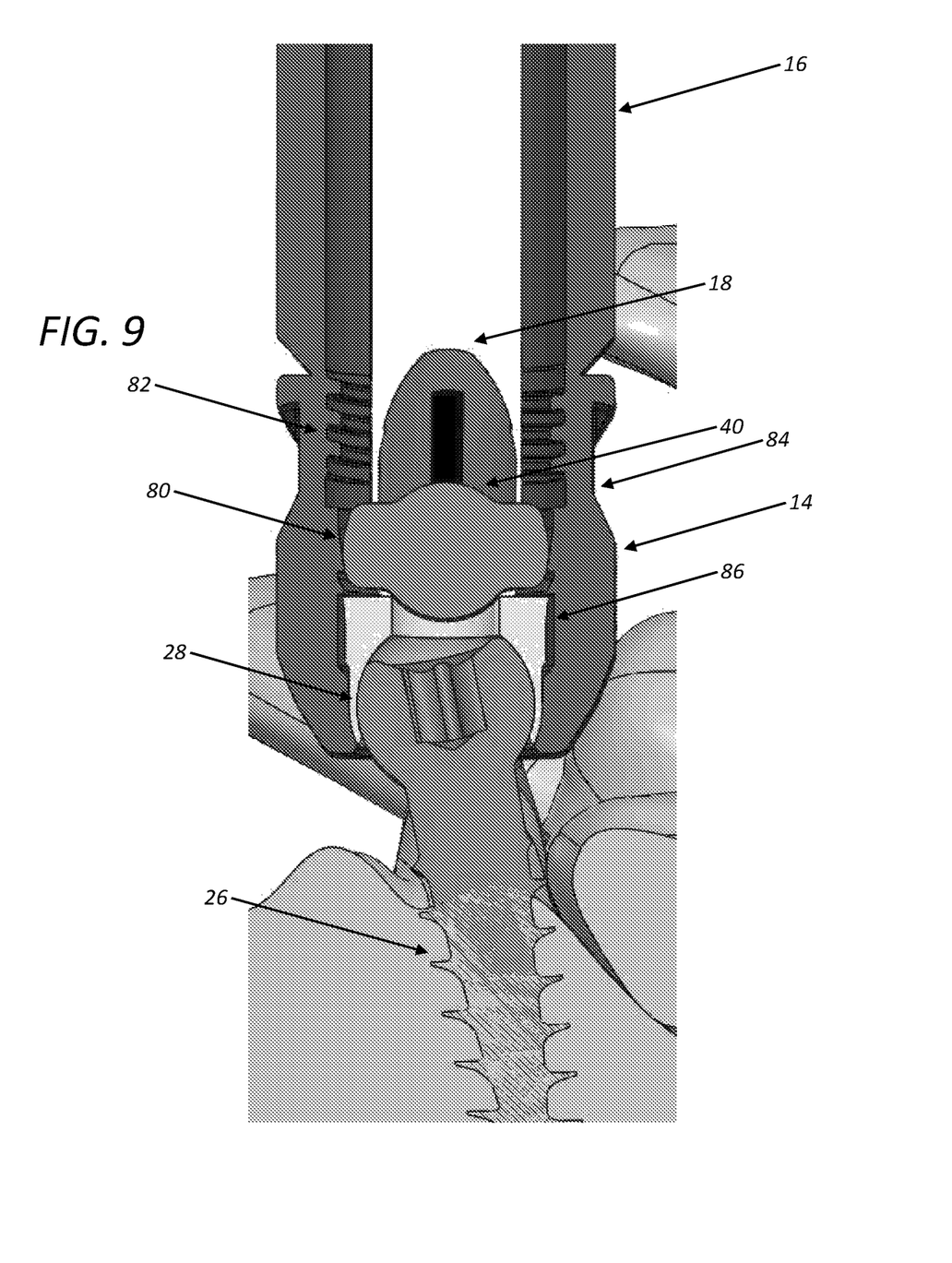
FIG. 9 is a partial cross-sectional view of one exemplary embodiment of the bone anchor, tab extenders, and rod of the present invention, highlighting the use of a retention collar to secure the head of the threaded screw.

Referring now specifically to FIG. 9, in one exemplary embodiment, once the partial spherical bearing 40 and the rod 18 are pivoted into position within the internal channel 80 of the head body 14, an externally-threaded set screw may be driven into the internally-threaded portion 82 of the internal channel 80 defined by the head body tabs 84, thereby biasing the rod 18 towards the head 28 of the screw 26. In this exemplary embodiment, a locking collar 86 is disposed between the partial spherical bearing 40 and the head 28 of the screw and partially about the head 28 of the screw 26. When the locking collar 86 is press fit into the internal channel 80 of the head body 14 by the partial spherical bearing 40 and the set screw, the lower portion of the locking collar 86 is compressed around the head 28 of the screw 26, thereby securing the head body 14 firmly to the head 28 of the screw 26. Accordingly, the upper surface of the locking collar 86 may be substantially conformal with the lower surface of the partial spherical bearing 40, defining a concave/convex surface, and the lower surface of the locking collar 86 may be substantially conformal with the upper surface of the head 28 of the screw 26, also defining a concave/convex surface.

Figure 10:
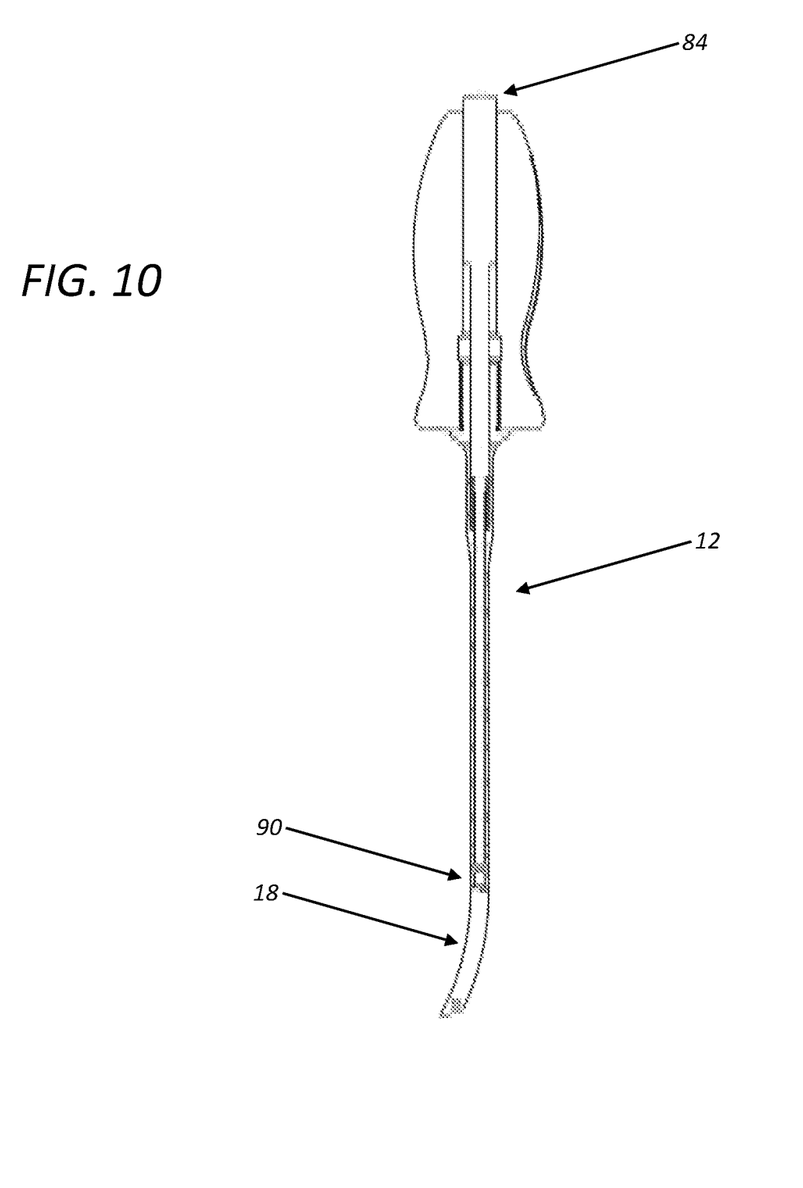
FIG. 10 is a planar view of another exemplary embodiment of the inserter tool of the present invention, coupled to a rod of the present invention.
Figure 11:
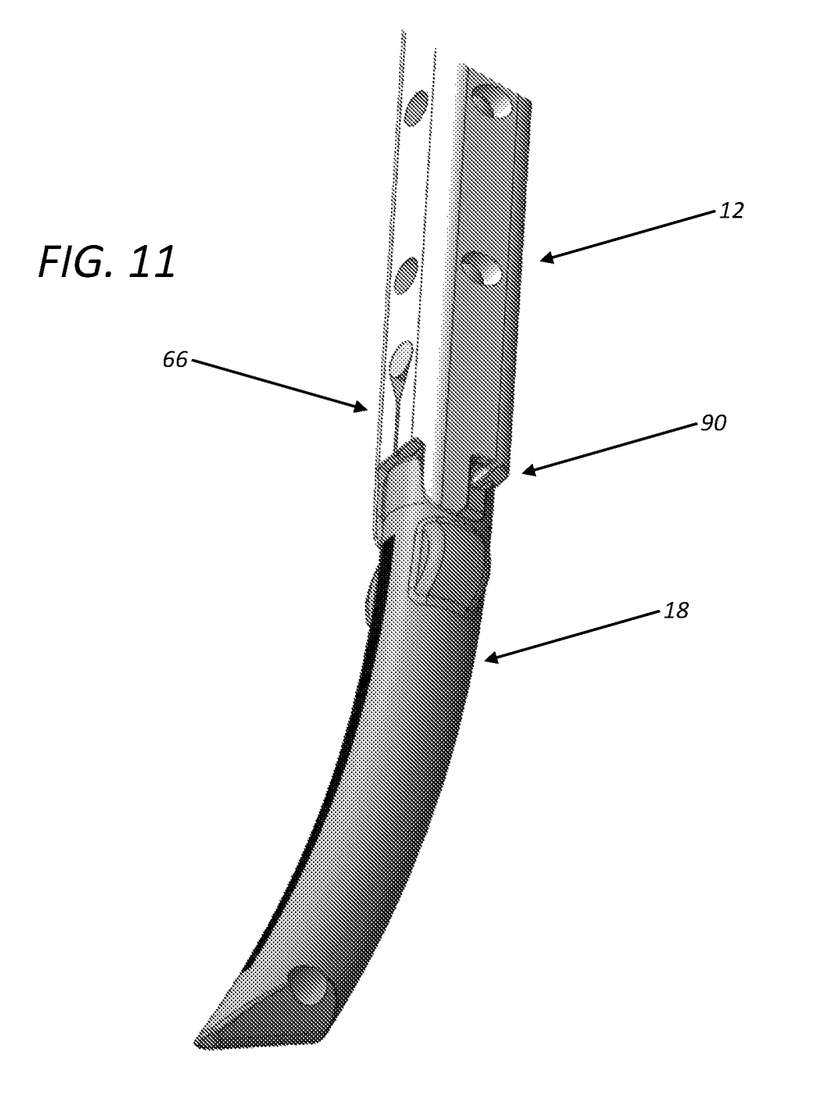
FIG. 11 is a partial perspective view of another exemplary embodiment of the inserter tool of the present invention, highlighting the rod engagement portion and splaying release mechanism.
Figure 12:
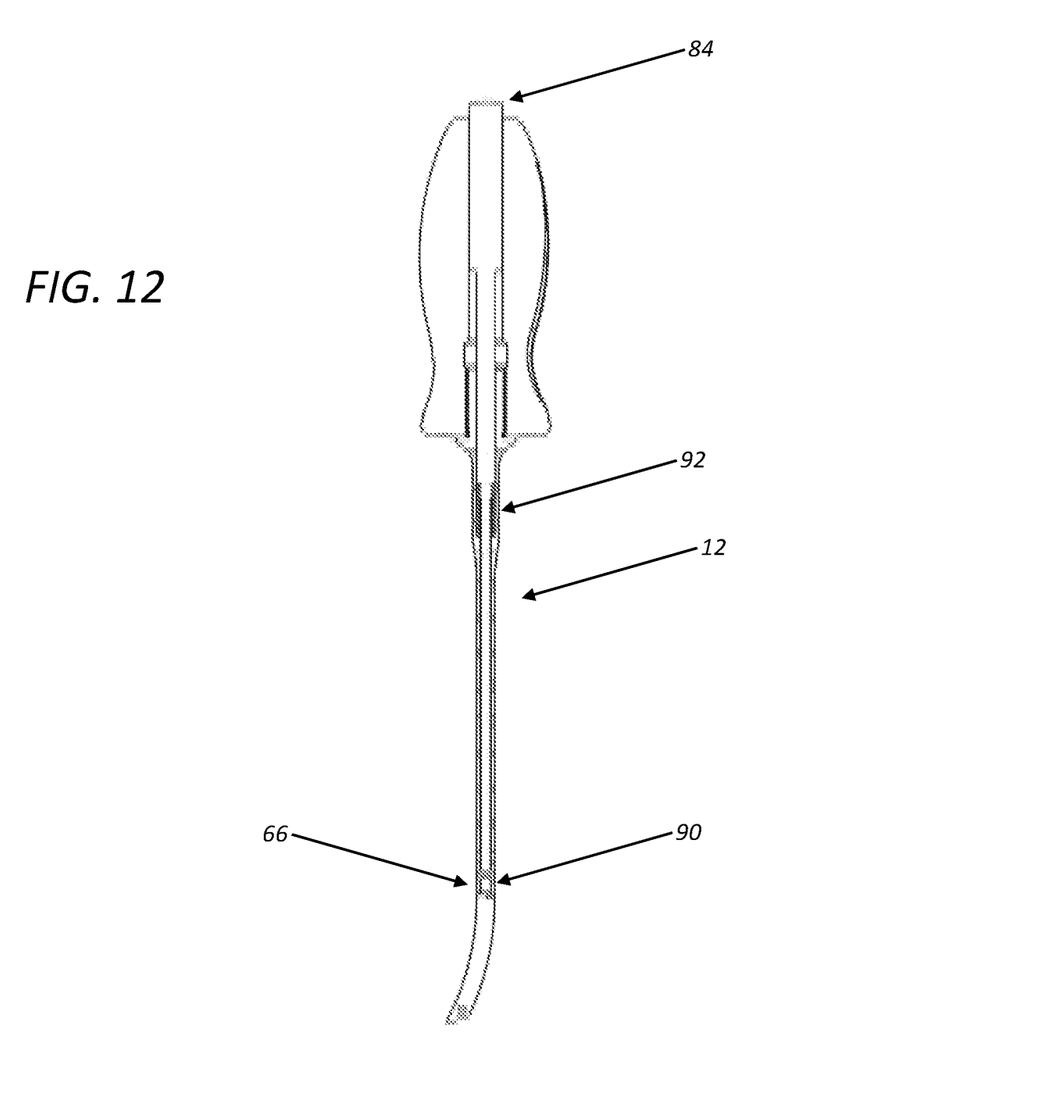
FIG. 12 is a cross-sectional view of another exemplary embodiment of the inserter tool of the present invention, highlighting the actuation of the splaying release mechanism.

FIGS. 10-12 illustrate another exemplary embodiment of the inserter tool 12 of the present invention, coupled to the rod 18 of the present invention. In this exemplary embodiment, a push button 88 or the like may be used to actuate the pivot mechanism 90 and/or the splaying mechanism 66, which operate in a similar manner as before. Again, the push button 88 may be biased by a spring 92 or the like.

Figure 13:
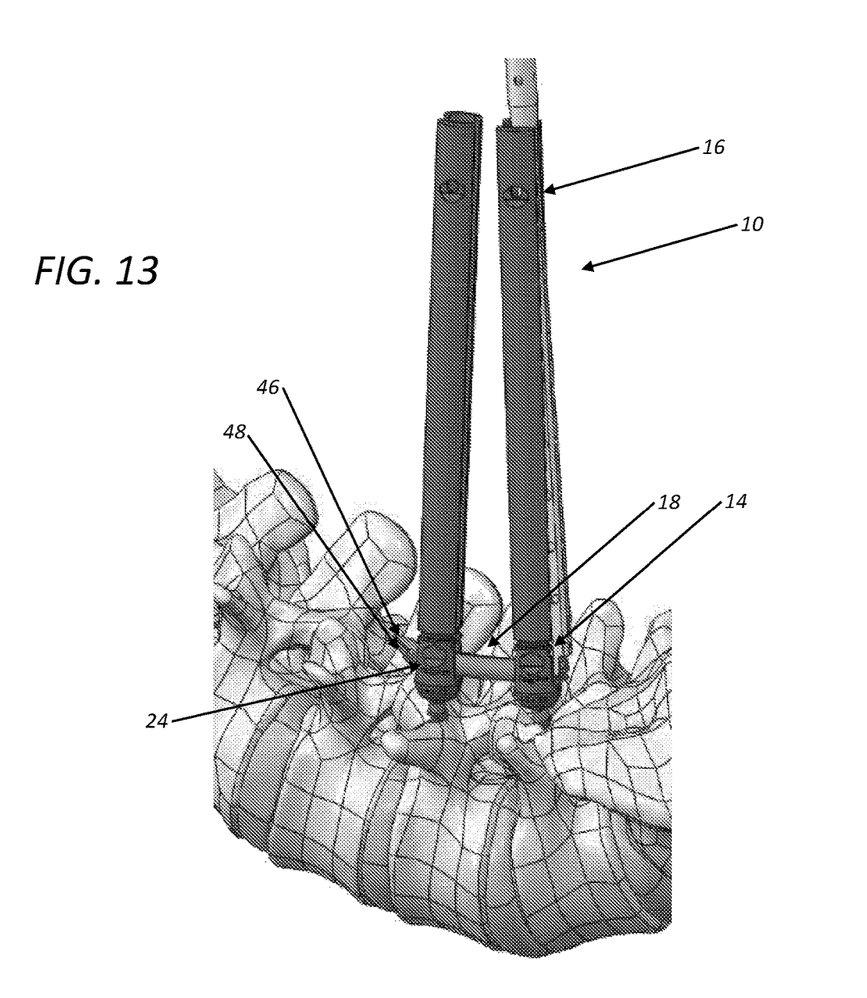
FIG. 13 is a partial perspective view of one exemplary embodiment of the MIS bone anchor and rod assembly and inserter tool of the present invention in a fully deployed configuration, highlighting the associated visualization mechanism.

FIG. 13 is a perspective view of one exemplary embodiment of the MIS bone anchor and rod assembly 10 of the present invention, incorporating a plurality of pedicle screws 24 and tab extenders 16 in a fully actuated configuration, with the rod 18 at the bottom of the associated tab extender 16 in the head body 14 and fully pivoted into the adjacent head body 14, with the tapered end 46 of the rod 18 including a holes 48 that may be visualized during a surgical procedure, by eye or under fluoroscopy, to determine that the rod 18 has sufficiently penetrated through the adjacent head body 14.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A bone stabilization assembly, comprising:
a bone anchor comprising a threaded screw comprising a head, a head body comprising a pair of opposed tabs coupled to the head of the screw, and a pair of opposed tab extenders selectively extending longitudinally from the pair of opposed tabs of the head body, wherein the pair of opposed tab extenders and the pair of opposed tabs define an internal longitudinal track and a longitudinal slot; and
a rod comprising an enlarged pivot joint that forms a partial spherical bearing at a proximal end thereof and an elongate portion at a distal end thereof, wherein the enlarged pivot joint of the rod is configured to be selectively disposed conformally within a partial spherical bearing formed by the pair of opposed tab extenders and the pair of opposed tabs and translated along the internal longitudinal track defined by the pair of opposed tab extenders and the pair of opposed tabs and the elongate portion of the rod is configured to selectively protrude through the longitudinal slot defined by the pair of opposed tab extenders and the pair of opposed tabs;

wherein, in a first configuration, the rod is distal from the head body and the elongate portion of the rod is disposed longitudinally within the internal longitudinal track defined by the pair of opposed tab extenders, and, in a second configuration, the rod is proximal to the head body and the elongate portion of the rod protrudes substantially perpendicularly from the longitudinal slot defined by the pair of opposed tabs.

2. The bone stabilization assembly of claim 1, wherein the rod is pivoted from the first configuration to the second configuration about the enlarged pivot joint as the enlarged pivot joint is translated along the internal longitudinal track and into the head body.

3. The bone stabilization assembly of claim 2, wherein the rod is translated along the internal longitudinal track and pivoted using an inserter tool that is selectively coupled to the proximal end of the rod.

4. The bone stabilization assembly of claim 3, wherein the inserter tool comprises an elongate shaft, and wherein a pair of opposed tines of the inserter tool selectively engage a pair of opposed holes manufactured into the proximal end of the rod and a pusher bar of the inserter tool selectively engages a pusher channel manufactured into the proximal end of the rod adjacent to the pair of opposed holes.

5. The bone stabilization assembly of claim 4, wherein the pusher bar of the inserter tool is configured to be selectively translated longitudinally along the elongate shaft with respect to the pair of opposed tines, thereby selectively translating the pusher channel of the rod along the internal longitudinal track with respect to the pair of opposed holes of the rod, thereby causing rotation of the rod about the enlarged pivot joint.

6. The bone stabilization assembly of claim 1, wherein, in the second configuration, the enlarged pivot joint comprises a cross-sectional shape that substantially matches an internal cross-sectional shape of the head body such that it fits conformally therein.

7. The bone stabilization assembly of claim 1, further comprising an externally-threaded set screw that is configured to selectively engage internal threads manufactured into the pair of opposed tabs of the head body, thereby biasing the rod into the head of the screw and securing the rod to the head body.

8. The bone stabilization assembly of claim 7, further comprising a retention collar disposed partially between the rod and the head of the screw.

9. The bone stabilization assembly of claim 8, wherein the retention collar is press fit into the head body and about the head of the screw when the rod is biased into the head of the screw.

10. The bone stabilization assembly of claim 1, wherein, in the second configuration, the elongate portion of the rod engages and is subsequently secured to a head body of an adjacent bone anchor.

* * * * *